US010246763B2

(12) United States Patent
Liu et al.

(10) Patent No.: US 10,246,763 B2
(45) Date of Patent: Apr. 2, 2019

(54) MAGNESIUM-ZINC-STRONTIUM ALLOYS FOR MEDICAL IMPLANTS AND DEVICES

(71) Applicant: The Regents of the University of California, Oakland, CA (US)

(72) Inventors: Huinan Liu, Riverside, CA (US); Aaron Cipriano, Riverside, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 435 days.

(21) Appl. No.: 13/975,881

(22) Filed: Aug. 26, 2013

(65) Prior Publication Data

US 2014/0093417 A1 Apr. 3, 2014

Related U.S. Application Data

(60) Provisional application No. 61/693,184, filed on Aug. 24, 2012.

(51) Int. Cl.
*A61F 2/00* (2006.01)
*C22C 23/00* (2006.01)
(Continued)

(52) U.S. Cl.
CPC ............... *C22C 23/00* (2013.01); *A61F 2/00* (2013.01); *A61L 27/04* (2013.01); *A61L 27/306* (2013.01);
(Continued)

(58) Field of Classification Search
CPC ........... A61F 2/00; A61L 27/306; A61L 27/04
(Continued)

(56) References Cited

U.S. PATENT DOCUMENTS

2004/0034409 A1 2/2004 Heublein et al.
2004/0073297 A1 4/2004 Rohde et al.
(Continued)

FOREIGN PATENT DOCUMENTS

CN 101869726 A * 10/2010

OTHER PUBLICATIONS

NPL-1: Brar et al, Investigation of the mechanical and degradation properties of MG—Sr and Mg—Zn—Sr alloys for use as potential biodegradable implant materials, J. of the Mechanical Behavior of Biomedical Materials 7 (2012), pp. 87-95, Published online Aug. 31, 2011.*

(Continued)

*Primary Examiner* — Jie Yang
(74) *Attorney, Agent, or Firm* — Buchanan Ingersoll & Rooney PC

(57) ABSTRACT

A medical implant and/or device, which includes a biodegradable and cytocompatible magnesium-zinc-strontium alloy is disclosed. The implant and/or device can include a biodegradable and cytocompatible magnesium-zinc-strontium (Mg—Zn—Sr) alloy having a weight percent composition of Zn and Sr as follows: $0.01 \leq Zn \leq 6$ wt %, $0.01 \leq Sr \leq 3$ wt %. A method for manufacturing an implant in the form of a biodegradable and cytocompatible magnesium-zinc-strontium alloy is disclosed, which includes melting the biodegradable and cytocompatible magnesium-zinc-strontium alloy in an inert environment and molding the biodegradable magnesium-zinc-strontium alloy in a semi-solid state.

14 Claims, 12 Drawing Sheets

(51) Int. Cl.
| | |
|---|---|
| *B22D 25/02* | (2006.01) |
| *C22C 23/04* | (2006.01) |
| *B21C 23/00* | (2006.01) |
| *A61L 27/04* | (2006.01) |
| *A61L 27/30* | (2006.01) |
| *A61L 27/58* | (2006.01) |
| *A61L 31/02* | (2006.01) |
| *A61L 31/08* | (2006.01) |
| *A61L 31/14* | (2006.01) |

(52) U.S. Cl.
 CPC ............ *A61L 27/58* (2013.01); *A61L 31/022* (2013.01); *A61L 31/088* (2013.01); *A61L 31/148* (2013.01); *B21C 23/00* (2013.01); *B22D 25/02* (2013.01); *C22C 23/04* (2013.01)

(58) Field of Classification Search
 USPC ........................................................ 420/411
 See application file for complete search history.

(56) References Cited

U.S. PATENT DOCUMENTS

| | | |
|---|---|---|
| 2005/0027350 A1 | 2/2005 | Momma et al. |
| 2005/0058688 A1 | 3/2005 | Boerger et al. |
| 2005/0266041 A1 | 12/2005 | Gerold et al. |
| 2006/0018954 A1 | 1/2006 | Kuttler |
| 2006/0020289 A1 | 1/2006 | Kuttler |
| 2006/0020315 A1 | 1/2006 | Geistert et al. |
| 2006/0020317 A1 | 1/2006 | Flach et al. |
| 2006/0052863 A1 | 3/2006 | Harder et al. |
| 2006/0052864 A1 | 3/2006 | Harder et al. |
| 2006/0064160 A1 | 3/2006 | Gerold et al. |
| 2006/0085081 A1 | 4/2006 | Shadduck et al. |
| 2006/0089715 A1 | 4/2006 | Truckai et al. |
| 2006/0246107 A1 | 11/2006 | Harder et al. |
| 2007/0003596 A1 | 1/2007 | Tittelbach et al. |
| 2007/0020306 A1 | 1/2007 | Schultheiss |
| 2007/0142899 A1 | 6/2007 | Lootz et al. |
| 2007/0191708 A1 | 8/2007 | Gerold et al. |
| 2007/0227629 A1 | 10/2007 | Gerold et al. |
| 2007/0299512 A1 | 12/2007 | Korzuschnik et al. |
| 2008/0033530 A1 | 2/2008 | Zberg et al. |
| 2008/0033531 A1 | 2/2008 | Barthel et al. |
| 2008/0033576 A1 | 2/2008 | Gerold et al. |
| 2008/0188927 A1 | 8/2008 | Rohde et al. |
| 2008/0249638 A1 | 10/2008 | Asgari |
| 2009/0018648 A1 | 1/2009 | Wittchow |
| 2009/0024211 A1 | 1/2009 | Wittchow |
| 2009/0030494 A1 | 1/2009 | Stefanadis et al. |
| 2009/0081313 A1 | 3/2009 | Aghion et al. |
| 2009/0132042 A1 | 5/2009 | Hetke et al. |
| 2009/0171452 A1 | 7/2009 | Yamamoto et al. |
| 2009/0198320 A1 | 8/2009 | Mueller et al. |
| 2009/0208555 A1 | 8/2009 | Kuttler et al. |
| 2009/0324682 A1 | 12/2009 | Popowski |
| 2010/0034899 A1 | 2/2010 | Harder et al. |
| 2010/0049300 A1 | 2/2010 | Harder |
| 2010/0075162 A1 | 3/2010 | Yang et al. |
| 2010/0076556 A1 | 3/2010 | Tomantschger et al. |
| 2010/0082092 A1 | 4/2010 | Gerold |
| 2010/0119576 A1 | 5/2010 | Harder et al. |
| 2010/0119582 A1 | 5/2010 | Boerger et al. |
| 2010/0137986 A1 | 6/2010 | Truckai et al. |
| 2010/0161054 A1 | 6/2010 | Park et al. |
| 2010/0174367 A1 | 7/2010 | Janko et al. |
| 2010/0305684 A1 | 12/2010 | Kim et al. |
| 2010/0324659 A1 | 12/2010 | Mews et al. |
| 2011/0034991 A1 | 2/2011 | Barthel et al. |
| 2011/0054629 A1 | 3/2011 | Seok et al. |
| 2011/0130823 A1 | 6/2011 | Gerold et al. |
| 2011/0172724 A1* | 7/2011 | Hort .................. A61L 24/0063 606/86 R |
| 2011/0192500 A1 | 8/2011 | Uggowitzer et al. |
| 2011/0213286 A1 | 9/2011 | Riesinger |
| 2011/0311456 A1 | 12/2011 | Zberg et al. |
| 2011/0319986 A1 | 12/2011 | Bayer et al. |
| 2012/0101566 A1 | 4/2012 | Mews et al. |
| 2012/0141596 A1 | 6/2012 | Lally |
| 2012/0156477 A1 | 6/2012 | Kurze et al. |
| 2012/0269673 A1 | 10/2012 | Koo et al. |

OTHER PUBLICATIONS

NPL: on-line translation of CN 101869726 A (Year: 2010).*
Ludeke et al., "Susceptibility Artefacts in NMR Imaging", Magnetic Resonance Imaging, 1985, vol. 3, pp. 329-343.
Ziats et al., "In vitro and in vivo interactions of cells with biomaterials", Biomaterials, Jan. 1988, vol. 9, pp. 5-13.
Bostman et al., "Foreign-Body Reactions to Fracture Fixation Implants of Biodegradable Synthetic Polymers", The Journal of Bone and Joint Surgery, Jul. 1990, vol. 72-B, No. 4, pp. 592-596.
Fosmire, "Zinc toxicity1,2", Am J Clin Nutr, 1990, vol. 51, pp. 225-227.
Laschinski et al., "Cytotoxicity Test Using Blastocyst-Derived Euploid Embryonal Stem cells: A New Approach to in Vitro Teratogenesis Screening", Reproductive Toxicology,1991, vol. 5, No. 1, pp. 57-64.
Breen et al., "Titanium Lines: A Manifestation of Metallosis and Tissue Response to Titanium Alloy Megaprostheses at the Knee", Clinical Radiology, 1993, vol. 47, pp. 274-277.
Pizzoferrato et al., "Cell Culture Methods for Testing Biocompatiblity", Clinical Materials, 1994, vol. 15, pp. 173-190.
Beuf et al., "Magnetic Resonance Imaging for the Determination of Magnetic Susceptibility of Materials", Journal of Magnetic Resonance, 1996, Series B 112, No. 0120, pp. 111-118.
Petersilge et al., "Optimizing Imaging Parameters for MR Evaluation of the Spine with Titanium Pedicle Screws", AJR, 1996, vol. 166, pp. 1213-1218.
Sidhu et al., "Intraarticular Migration of a Femoral Interference Fit Screw A Complication of Anterior Cruciate Ligament Reconstruction", The American Journal of Sports Medicine, 1997, vol. 25, No. 2, pp. 268-271.
Takizawa et al. "Foreign Body Gonitis Caused by a Broken Poly-L-Lactic Acid Screw", The Journal of Arthroscopic and Related Surgery, Apr. 1998, vol. 14, No. 3, pp. 329-330.
Zhang et al., "An Investigation of the Properties of Mg—Zn—Al Alloys", Scripta Materialia, 1998, vol. 39, No. 1, pp. 45-53.
Maeng et al., "Microstructure and Strength of Rapidly Solidified and Extruded Mg—Zn Alloys", Scripta mater, 2000, vol. 43, No. 5, pp. 385-389.
Dahl et al., "Incorporation and Distribution of Strontium in Bone", Bone, Apr. 2001, vol. 28, No. 4, pp. 446-453.
Eiges et al., "Establishment of human embryonic stem cell-transfected clones carrying a marker for undifferentiated cells", Current Biology, 2001, vol. 11, No. 7, pp. 514-518.
Marie et al., "Mechanisms of Action and Therapeutic Potential of Strontium in Bone", Calcified Tissue International, 2001, vol. 69, pp. 121-129.
Shafer et al., "Broken Poly-L-Lactic Acid Interference Screw After Ligament Reconstruction", The Journal of Arthroscopic and Related Surgery, Sep. 2002, vol. 18, No. 7, pp. 1-4.
Hidaka et al., "Chamber-specific differentiation of Nkx2.5-positive cardiac precursor cells from murine embryonic stem cells", The FASEB Journal, Feb. 19, 2003, vol. 17, No. 6. (pp. 22).
Smith et al., "Fracture of Bilok Interference Screws on Insertion During Anterior Cruciate Ligament Reconstruction", The Journal of Arthroscopic and Related Surgery, Nov. 2003, vol. 19, No. 9, pp. e115-e117.
Davila et al., "Use and Application of Stem Cells in Toxicology",Toxicological Sciences, 2004, vol. 79, pp. 214-223.
Meunier et al., "The Effects of Strontium Ranelate on the Risk of Vertebral Fracture in Women with Postmenopausal Osteoporosis", The New England Journal of Medicine, Jan. 29, 2004, vol. 350, pp. 459-468.
Lembeck et al., "Severe cartilage damage by broken poly-L-lactic acid (PLLA) interference screw after ACL reconstruction", Knee Surg Sports Traumatol Arthrosc, 2005, vol. 13, pp. 283-286.

(56) References Cited

OTHER PUBLICATIONS

Baums et al., "Intraarticular migration of a broken biodegradable interference screw after anterior cruciate ligament reconstruction", Knee Surg Sports Traumatol Arthrosc, 2006, vol. 14, pp. 865-868.
Marie, "Strontium ranelate: A physiological approach for optimizing bone formation and resorption", Bone, 2006, vol. 38, pp. S10-S14.
Somekawa et al., "Effect of solid-solution strengthening on fracture toughness in extruded Mg—Zn alloys", Scripta Materialia, 2006, vol. 55, pp. 593-596.
Staiger et al., "Magnesium and its alloys as orthopedic biomaterials: A review", Biomaterials, 2006, vol. 27, pp. 1728-1734.
Gao et al., "Characterization of strengthening precipitate phases in a Mg—Zn alloy", Scripta Materialia, 2007, vol. 56, pp. 645-648.
Walton et al., "Long-term in vivo Degradation of Poly-L-lactide (PLLA) in Bone", Journal of Biomaterials Applications, Apr. 2007, vol. 21, pp. 395-411.
Adler et al., "First steps in establishing a developmental toxicity test method based on human embryonic stem cells", Toxicology in Vitro, 2008, vol. 22, pp. 200-211.
Kwak et al., "Delayed Intra-articular Inflammatory Reaction Due to Poly-L-Lactide Bioabsorbable Interference Screw Used in Anterior Cruciate Ligament Reconstruction", The Journal of Arthroscopic and Related Surgery, Feb. 2008, vol. 24, No. 2, pp. 243-246.
Liu et al., "Refinement role of electromagnetic stifling and strontium in AZ91 magnesium alloy", Journal of Alloys and Compounds, 2008, vol. 450, pp. 546-550.
Rettig et al., "Composition of corrosion layers on a magnesium rare-earth alloy in simulated body fluids", Journal of Biomedical Materials Research Part A, 2009, vol. 88, pp. 359-369.
Witte et al., "Degradable biomaterials based on magnesium corrosion", Current Opinion in Solid State and Materials Science, 2008, vol. 12, pp. 63-72.
Xin et al.,"Influence of aggressive ions on the degradation behavior of biomedical magnesium alloy in physiological environment", Acta Biomaterialia, 2008, vol. 4, pp. 2008-2015.
Xu et al., "In vitro corrosion behaviour of Mg alloys in a phosphate buffered solution for bone implant application", J Mater Sci: Mater Med, 2008, vol. 19, pp. 1017-1025.
Yang et al., "Effect of Mg—10Sr master alloy on grain refinement of AZ31 magnesium alloy", Materials Science and Engineering A, 2008, vol. 491, pp. 440-445.
Tran et al., "Nanotechnology for bone materials", Wiley Interdiscip Rev Nanomed Nanobiotechnol, May/Jun. 2009, vol. 1, pp. 336-351.
Feyerabend et al., "Evaluation of short-term effects of rare earth and other elements used in magnesium alloys on primary cells and cell lines", Acta Biomaterialia, 2010, vol. 6, pp. 1834-1842.
West et al., "Predicting human developmental toxicity of pharmaceuticals using human embryonic stem cells and metabolomics", Toxicology and Applied Pharmacology, 2010, vol. 247, pp. 18-27.
Witte, "The history of biodegradable magnesium implants: A review", Acta Biomaterialia, 2010, vol. 6, pp. 1680-1692.
Abidin et al., "Corrosion of high purity Mg, AZ91, ZE41 and Mg2Zn0.2Mn in Hank's solution at room temperature", Corrosion Science, 2011, vol. 53, pp. 862-872.
Johnson et al., "In vitro evaluation of the surface effects on magnesium-yttrium alloy degradation and mesenchymal stem cell adhesion", J Biomed Mater Res Part A, Feb. 2012, vol. 100A, No. 2, pp. 477-485.
Liu, "The effects of surface and biomolecules on magnesium degradation and mesenchymal stem cell adhesion", Journal of Biomedical Materials Research A, Nov. 2011, vol. 99A, No. 2, pp. 249-260.
Seiler et al., "The validated embryonic stem cell test to predict embryotoxicity in vitro", Nature Protocols, 2011, vol. 5, No. 7, pp. 961-978.
Talbot et al., "Mouse and Human Embryonic Stem Cells: Can They Improve Human Health by Preventing Disease?", Current Topics in Medicinal Chemistry, 2011, vol. 11, No. 13, pp. 1638-1652.
Borkar et al., "Effect of strontium on flow behavior and texture evolution during the hot deformation of Mg-1 wt%Mn alloy", Materials Science and Engineering A, 2012, vol. 537, pp. 49-57.
Gu et al., "In vitro and in vivo studies on a Mg—Sr binary alloy system developed as a new kind of biodegradable metal", Acta Biomaterialia, 2012, vol. 8, pp. 2360-2374.
Guan et al., "Electrodeposition of hydroxyapatite coating on Mg—4.0Zn—1.0Ca—0.6Zr alloy and in vitro evaluation of degradation, hemolysis, and cytotoxicity", Journal Of Biomedical Materials Research A, Apr. 2012, vol. 100A, No. 4, pp. 999-1015.
Guan et al., "Development and evaluation of a magnesium-zinc-strontium alloy for biomedical applications—Alloy processing, microstructure, mechanical properties, and biodegradation", Materials Science and Engineering C, 2013, vol. 33, pp. 3661-3669.
A. F. Cipriano et al., "Cytocompatibility and early inflammatory response of human endothelial cells in direct culture Mg—Zn—Sr alloys", Acta Biomaterialia, Elsevier, Ltd. 2016 (22 pages).

\* cited by examiner

MAGNESIUM-ZINC-STRONTIUM ALLOYS FOR MEDICAL IMPLANTS AND DEVICES

CROSS-REFERENCE TO RELATED APPLICATIONS

This application claims the benefit of U.S. Provisional Patent Application Ser. No. 61/693,184, filed Aug. 24, 2013, the entire contents of which are hereby incorporated herein by reference.

FEDERALLY SPONSORED RESEARCH OR DEVELOPMENT

This invention was made with Government support under Grant No. 1125801, awarded by the National Science Foundation. The Government has certain rights in this invention.

FIELD

This disclosure relates to Magnesium-Zinc-Strontium (Mg—Zn—Sr) alloys for medical implant and/or devices, and a method of manufacturing the Magnesium-Zinc-Strontium (Mg—Zn—Sr) alloys for medical implants and/or devices.

BACKGROUND

Recent studies on Magnesium (Mg) alloys have shown their potential as a novel class of biodegradable metallic materials for medical applications, particularly as orthopedic and maxillofacial implants. Materials currently used for these implants include non-degradable metals (e.g., titanium alloys) and bioabsorbable polymers. Although titanium alloys are widely used, their major limitations include stress shielding on surrounding bone, necessity of revision surgeries for implant removal, and distortion on post-operative evaluation by magnetic resonance imaging (MRI). Moreover, these permanent metals release harmful wear particulates, causing implant loosening and failure in the end. In contrast, bioabsorbable polymers, while degradable, often lack the mechanical strength needed for load bearing implants. Breakage of polymeric implants has been reported during and after surgeries, which complicates patient recovery and causes liability concerns. Bioabsorbable polymers also produce acidic degradation products that further contribute to implant failure and tissue inflammation.

The main advantages of Mg-based implants lie in the biodegradable and resorbable nature of Mg, where degradation products of Mg can be excreted or used in metabolic processes, and its similar mechanical properties to cortical bone. Magnesium is one of the most abundant cations in intracellular and extracellular fluids in the body and is essential for bone and tooth formation. The level of Mg in the extracellular fluid ranges between 0.7 and 1.05 mmol/L, where homeostasis is maintained by the kidney and intestine. Although Mg is a promising material for load bearing medical implant applications, it degrades much too rapidly in physiological conditions to meet the clinical requirements. The degradation rate of Mg alloys should be slow enough so that the load bearing properties of the implants are not compromised prior to tissue regeneration. Rapid degradation causes premature mechanical failure or detachment of implants and an increase in local pH. Mg-based alloys have been actively explored and reported to decrease the rapid degradation compared to pure Mg, while promoting mechanical properties and retaining osteoconductivity leading to enhanced bone formation. Therefore, Mg-based alloys should be further studied and optimized to improve biodegradation, bioactivity, biocompatibility, and mechanical properties for orthopedic and maxillofacial implants.

SUMMARY

In accordance with an exemplary embodiment, a medical implant and/or device comprises: a biodegradable and cytocompatible magnesium-zinc-strontium alloy.

In accordance with another exemplary embodiment, the biodegradable and cytocompatible magnesium-zinc-strontium (Mg—Zn—Sr) alloy has a weight percent composition of Zn and Sr as follows: $0.01 \leq Zn \leq 6$ wt %, $0.01 \leq Sr \leq 3$ wt %.

In accordance with a further exemplary embodiment, a method for manufacturing an implant in the form of a biodegradable and cytocompatible magnesium-zinc-strontium alloy, comprises: melting the biodegradable and cytocompatible magnesium-zinc-strontium alloy in an inert environment, and molding the biodegradable magnesium-zinc-strontium alloy in a semi-solid state.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

FIG. 2(A) is a scanning electron micrograph of ZSr41C at a 25 kV accelerating voltage with a magnification of 25,000×. Scale bar=2 µm.

DETAILED DESCRIPTION

Figure 1:
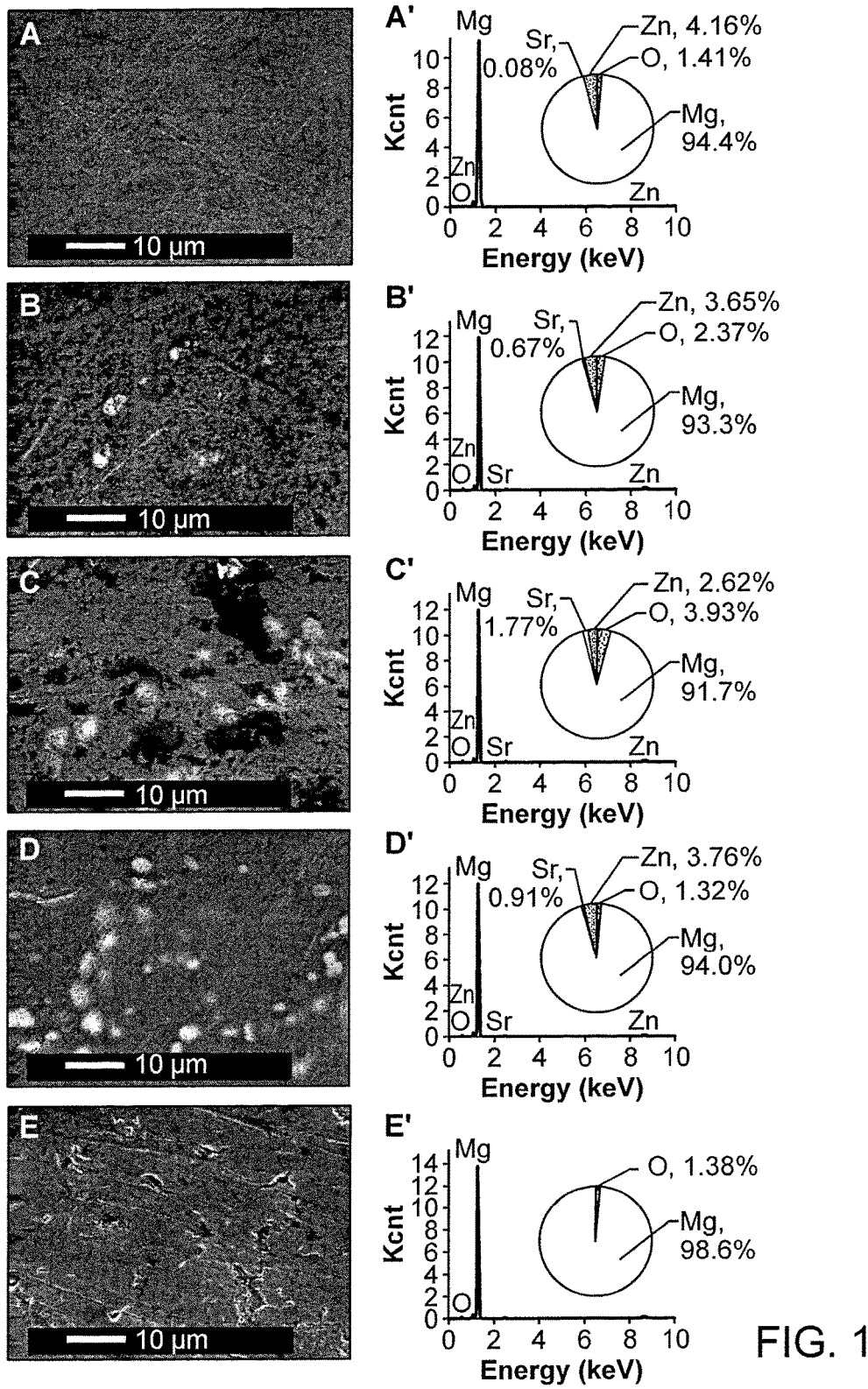
FIGS. 1(A)-(E) are scanning electron micrographs of (A) ZSr41A, (B) ZSr41B, (C) ZSr41C, (D) ZSr41 D, and (E) P-Mg after surface polishing at a magnification of 5,000×. (A'-E') EDS spectra and surface elemental composition (wt. %) of (A') ZSr41A, (B') ZSr41B, (C') ZSr41C, (D') ZSr41 D, and (E') P-Mg. Accelerating voltage was 25 kV. Scale bars=10 µm.

In accordance with an exemplary embodiment, the effects of alloying Mg with Zinc (Zn) and distinct amounts of Strontium (Sr) on improving the alloy degradation properties and cellular interactions compared to pure Mg were explored. The design of the Mg alloy composition can potentially control its grain size, surface microstructure, degradation, mechanical properties, cellular interactions, and successful tissue-implant integration. In previous studies, it has been shown that alloying Zn and Sr to Mg (ZSr41 alloy) resulted in an alloy with improved mechanical and corrosion properties compared to pure Mg. The improvement of properties resulted in part from grain refinement induced by dispersion of intermetallic compounds, namely Zn13Sr, which was formed due to the addition of both Zn and Sr as alloying elements. Furthermore, 4.0-6.0 wt. % Zn has been shown to be optimal for maximizing material strength and corrosion resistance, which was induced by strengthening effects of the intermetallic MgZn phase. In addition to the physiochemical advantages of adding Zn and Sr as alloying elements, Zn was selected because it is an important element in the body and participates in the syntheses of enzymes. Similarly, Sr can be added because it has similar chemical characteristics as Calcium (Ca), and accumulates mainly in trabecular bones. In addition, Sr has been proven to be beneficial for increasing bone mass and structural integrity in osteoporotic patients and its addition to hydroxyapatite cements has been shown to improve cement degradation and biocompatibility properties.

An in vitro cytocompatibility study was designed based on H9 human embryonic stem cells (hESC) to assess degradation and subtle cellular effects of four distinct ZSr41 alloys in comparison with pure Mg. The H9 hESC model was used to simulate physiological environment because of its greater sensitivity to known toxicants. The sensitive H9 hESC in vitro model can potentially improve the detection or screening of toxicological effects of new biomaterials by monitoring cell adhesion, proliferation, and differentiation. The use of in vitro hESC model in this disclosure was inspired by the successful implementation and validation of the embryonic stem cell test (EST), which was based on mouse ESC (mESC). The EST took advantage of mESC sensitivity to more accurately predict the toxicity of new compounds. Additional benefits of the H9 hESC-based model include availability, unlimited proliferation ability and the ease of genetic modification. In vitro gene modification techniques, such as gene transfection to express green fluorescent protein (GFP), enable cell sorting and evaluation of differentiation for downstream applications. Furthermore, since the degradation rate and mode of Mg are responsive to dissolved ions and other components in the surrounding solution, cell culture media provides a physiologically relevant model to test degradation of Mg-based alloys.

In accordance with an exemplary embodiment, Magnesium (Mg) alloys have attracted great interest for medical applications due to their unique biodegradable capability and desirable mechanical properties. When designed for medical applications, these alloys should have suitable degradation properties, for example, their degradation rate should not exceed the rate at which the degradation products can be excreted from the body. Cellular responses and tissue integration around the Mg-based implants are critical for clinical success. Four Magnesium-Zinc-Strontium (ZSr41) alloys were developed in this disclosure. The degradation properties of the ZSr41 alloys and their cytocompatibility were studied using an in vitro human embryonic stem cell (hESC) model due to the higher sensitivity of hESCs to known toxicants which allows the alloys to potentially detect toxicological effects of new biomaterials at an early stage. In accordance with an exemplary embodiment, four distinct ZSr41 alloys with 4 wt. % Zinc (Zn) and a series of Strontium (Sr) compositions (0.15 wt. %, 0.5 wt. %, 1 wt. %, and 1.5 wt. % Sr) were produced through metallurgical processing. Their degradation was characterized by measuring total weight loss of samples and pH change in the cell culture media. The concentration of Mg ions released from ZSr41 alloy into the cell culture media was analyzed using inductively coupled plasma atomic emission spectroscopy (ICP-AES). Surface microstructure and composition before and after culturing with hESCs were characterized using field emission scanning electron microscopy (FESEM) and energy dispersive X-ray spectroscopy (EDS). Pure Mg was used as a control during cell culture studies. For example, the Mg—Zn—Sr alloy with 0.15 wt. % Sr provided slower degradation and improved cytocompatibility as compared with pure Mg control.

In accordance with an embodiment, the disclosure presents a comparison of the degradation and cytocompatibility of four distinct Mg ZSr41 alloys in contact with cell culture media as compared with pure polished Magnesium (P-Mg)

control. In accordance with an exemplary embodiment, the ZSr41 alloys were composed of 94.5-95.85 wt. % Mg, 4 wt. % Zn and 0.15-1.5 wt. % Sr.

Preparation of Mg—Zn—Sr Alloys (ZSr41) and Mg Control

In accordance with an exemplary embodiment, the amount of Strontium present in each alloy, for example, was as follows: 0.15 wt. % Sr for ZSr41A; 0.5 wt. % Sr for ZSr41B; 1.0 wt. % Sr for ZSr41C; and 1.5 wt. % Sr for ZSr41 D. These alloys were produced by a metallurgical process consisting of melting, casting, rolling, and heat treatment. First, a stainless steel crucible was preheated to approximately 690-700° C., and then argon gas was blown into the stainless steel crucible. Pure Mg ingots with a purity of 99.9% were heated and melted in the stainless steel crucible. Argon gas with a flow rate of 6 L/min was blown into the alloy during heating and melting to protect the alloy from oxidation. After the Mg ingots melted, preheated metallic Zn and Sr were added into the magnesium and the mixture was stirred slightly to make the alloy elements react sufficiently. After the melting process, the alloy was held at 690-700° C. for 30 min, deslagged, and cast as ingots at 720° C. The ingots were rolled at 380° C. into sheets with a thickness of 1 mm. The alloy sheets were then aged at 175° C. for approximately 4 to 16 hrs. The produced ZSr41 alloy sheets were cut to 5×5 mm squares using a notcher (Model No. 100, Whitney Metal Tools Co.) for degradation and cell studies. Control P-Mg (as rolled, Goodfellow Co.) sheets of 99.9% purity and thickness of 250 µm were cut into 5×5 mm squares as well for degradation and cell studies.

Samples of ZSr41A, B, C, D and P-Mg were all prepared according to the following procedures: first, 5×5 mm squares were polished using 600, 800, and 1200 grit silicon carbide abrasive papers (Ted Pella, Inc.) to remove surface oxides. After surface polishing, ZSr41 and P-Mg samples had a silver-white color. Each sample was subsequently ultrasonically cleaned (VWR, Model 97043-036) for approximately 15 minutes in 200 proof ethanol (Koptec), individually weighed ($M_0$), and disinfected under ultraviolet (UV) radiation in a class II biosafety cabinet for 4 hours on each side prior to degradation and cell culture experiments.

Surface Characterization of ZSr41 Alloys Prior to Cell Culture

Prior to cell culture, the surface microstructures of ZSr41A, ZSr41B, ZSr41C, ZSr41 D, and P-Mg were characterized using a field emission scanning electron microscope (FESEM; Philips XL-30). Surface composition and elemental distribution were analyzed using energy dispersive X-ray spectroscopy (EDS; EDAX). An accelerating voltage of 25 kV was used to obtain SEM images and perform EDS analysis.

H9 Human Embryonic Stem Cell Culture

H9 human embryonic stem cells (H9 hESCs) were stably transfected with green fluorescence protein (GFP) at the octamer-binding transcription factor 4 (OCT4) promoter site using Gene Juice (Novagen), knockout Dulbecco's modified eagle's medium (KO-DMEM/F12; Invitrogen) and plasmid pCAG-eGFP-Internal Ribosome entry site (IRES)-Puromycin-R. For example, these transfected hESCs can be closely monitored for differentiation under fluorescence microscope. Feeder-free conditions in a T-25 flask (Falcon) with Geltrex™ matrix (Invitrogen) and mTeSR® 1 media (STEMCELL Technologies) were used to maintain the H9-OCT4 hESCs. Upon verification of 80-90% confluency under light microscope, the H9-OCT4 hESCs were passaged using Accutase (Innovative Cell Technologies) in conjunction with glass beads to provide gentle mechanical detachment.

Morphology and fluorescence of H9-OCT4 hESCs was observed using a fluorescence microscope (Nikon Eclipse Ti) to help ensure hESCs were normal and healthy prior to the co-culture with Mg alloys. Cell morphology was determined using phase contrast images. Fluorescent images were used to determine whether the hESCs differentiated or not. Phase contrast images and fluorescence images were merged using NIS-Elements Imaging Software (Nikon).

Culturing of H9-OCT4 hESCs with ZSr41 Alloys

The immersion method was used to investigate ZSr41 alloy and P-Mg degradation. Two 12-well plates (BD Falcon) were prepared by covering the wells with cold Geltrex™ matrix (Invitrogen) in DMEM media (Invitrogen 11965092) (1:50) for 24 hours. The excess Geltrex™ solution was aspirated and H9-OCT4 ESCs were seeded (passage 15) onto the wells with mTeSR® 1 media and maintained for 24 hours under standard cell culture conditions (that is, a sterile, 37° C., 5% $CO_2$/95% air, humidified environment).

After the initial 24-hour incubation period, the mTeSR® 1 media was removed and replenished with fresh media. The ZSr41A, B, C and D samples and Mg controls were placed into trans-well inserts (Corning) and positioned within the wells where H9-OCT4 ESCs were cultured. Positive control for cytocompatibility consisted of mTeSR® 1 media with H9-OCT4 hESCs only. The hESCs with Mg alloy samples and controls were then incubated in the Nikon Biostation CT under standard cell culture conditions. The mTeSR® 1 media was replaced with fresh media every 24 hours to more closely mimic in vivo conditions where the circulation system regularly takes away soluble degradation products from the local site of implantation. All degradation and cell culture experiments were performed in triplicate.

In Vitro Degradation of ZSr41 Alloys

Following preparation, the samples were incubated for a total of 72 hours (h). In order to more closely mimic in vivo conditions where the circulatory system regularly removes soluble degradation products from the local implantation site, incubation intervals were set as 24 hour. At each prescribed incubation interval, the culture media was removed and collected to measure pH levels and ionic concentrations. After the media collection, the same amount of fresh culture media was added into each well under sterile conditions. Caution was taken in order to help avoid disrupting degradation products on the specimen surface while removing the culture media along with any soluble degradation products found within. The pH levels were measured using a calibrated pH meter (VWR, Model SB70P) after each prescribed incubation interval. The concentration of Mg ions in the collected media was measured using inductively coupled plasma atomic emission spectroscopy (ICP-AES; Perkin Elmer Optima 2000 DV). Ionic concentrations were obtained from comparison with a standard curve generated from known concentration samples of $MgCl_2.6H_2O$ at 250, 125, 62.5, 31.25, and 15.63 ppm. Oversaturated media samples were diluted with DI water to obtain values within the range of the standard curve. At the end of the 72 hours incubation period, each sample was individually weighed ($M_f$) and the values were used to calculate mass loss per exposed unit area with respect to incubation time using the following equation:

$$(M_0-M_f)/(L*W+2*L*t+2*W*t)=M_{loss} \qquad (1)$$

where $M_0$ is initial sample weight, $M_f$ is final sample weight, L is sample length (5 mm), W is sample width (5 mm) and t is sample thickness (1 mm for ZSr41 and 250 μm for P-Mg).

In Vitro Cytocompatibility of ZSr41 Alloys with hESCs

Phase contrast and fluorescence images of two random points of each well were captured using Nikon Biostation CT at every 6 hour interval to evaluate cell viability in response to ZSr41 and Mg degradation products throughout the total 72 hour incubation period. The hESCs were continuously observed during the 72 hour incubation period to obtain detailed information on dynamic cellular responses corresponding to the early-stage implant performance in vivo. Cellular responses to the implants immediately after insertion are critical for the long-term success of implants, and, therefore, should be closely monitored. Nikon Biostation enabled the continuous in situ imaging of hESCs co-cultured with ZSr41 alloys and controls. The area of viable H9 hESCs showing positive OCT4 stem cell marker in images were outlined manually in ImageJ software. Numerical data of cell coverage for each sample was subsequently normalized against initial (t=0) cell coverage areas in order to monitor the change of viable cell coverage over time.

Surface Characterization of ZSr41 Alloys after Cell Culture

After 72 hours of cell culture, the surfaces of ZSr41A, ZSr41B, ZSr41C, ZSr41 D, and P-Mg were characterized using the SEM (Philips XL-30) at a 25 kV accelerating voltage. Sample surface composition and elemental distribution was analyzed using EDS at the 25 kV accelerating voltage.

Statistical Analyses

In vitro degradation and cytocompatibility experiments were run in triplicate. Parametric numerical data sets were analyzed using standard analysis of variance (ANOVA), whereas non-parametric numerical data sets were analyzed using Kruskal-Wallis analysis, both followed by standard post hoc tests with the Holm-Bonferroni correction; statistical significance was considered at $p<0.05$.

Surface Morphology and Composition of ZSr41 Alloys

Figure 2:
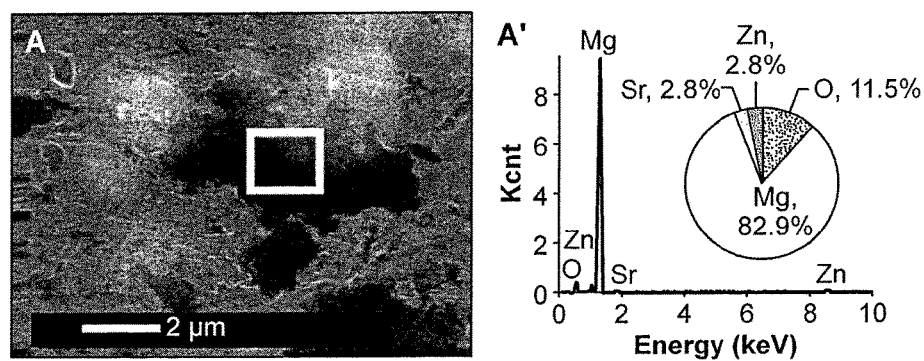
FIG. 2(A') is an EDS spectrum and surface elemental composition (wt. %) of the highlighted area on the ZSr41C surface.

Scanning electron micrographs of the four ZSr41 alloys before in vitro degradation showed different surface topography (FIG. 1, A-E). Different amounts, sizes, and distribution of a precipitated phase (white particles) were observed on the surfaces of ZSr41B, C, and D. Precipitate size ranged from 1 to 5 μm and the amount present on the alloys increased in this order: ZSr41B<ZSr41C<ZSr41 D. In contrast, there were no precipitates observed on ZSr41A and P-Mg. The darker regions visible in SEM images of the samples showed a higher amount of Oxygen (O), indicating the formation of an oxide layer (FIG. 2). Additionally, micron-sized pores were visible on the surface of P-Mg, but not on the surfaces of any of the ZSr41 alloys. Overall, the surface of the samples appeared smooth, but residual trace lines induced by polishing were visible on the surfaces.

EDS spectra and quantitative analyses at 5,000× magnification confirmed increasing levels of Sr in the ZSr41 alloys in the following order: ZSr41A<ZSr41B<ZSr41C (FIG. 1, A'-E' EDS spectra). All ZSr41 alloys had close to 4 wt. % Zn according to EDS quantitative analyses. EDS analyses also confirmed the presence of Mg on the surface of all ZSr41 alloys, as seen through the prevalent peak near 1.25 keV on all spectra. A low percentage of O (less than 4 wt. % on all samples) was found in all four ZSr41 alloys and P-Mg surfaces, indicating the presence of an oxide layer even after polishing.

Figure 3:
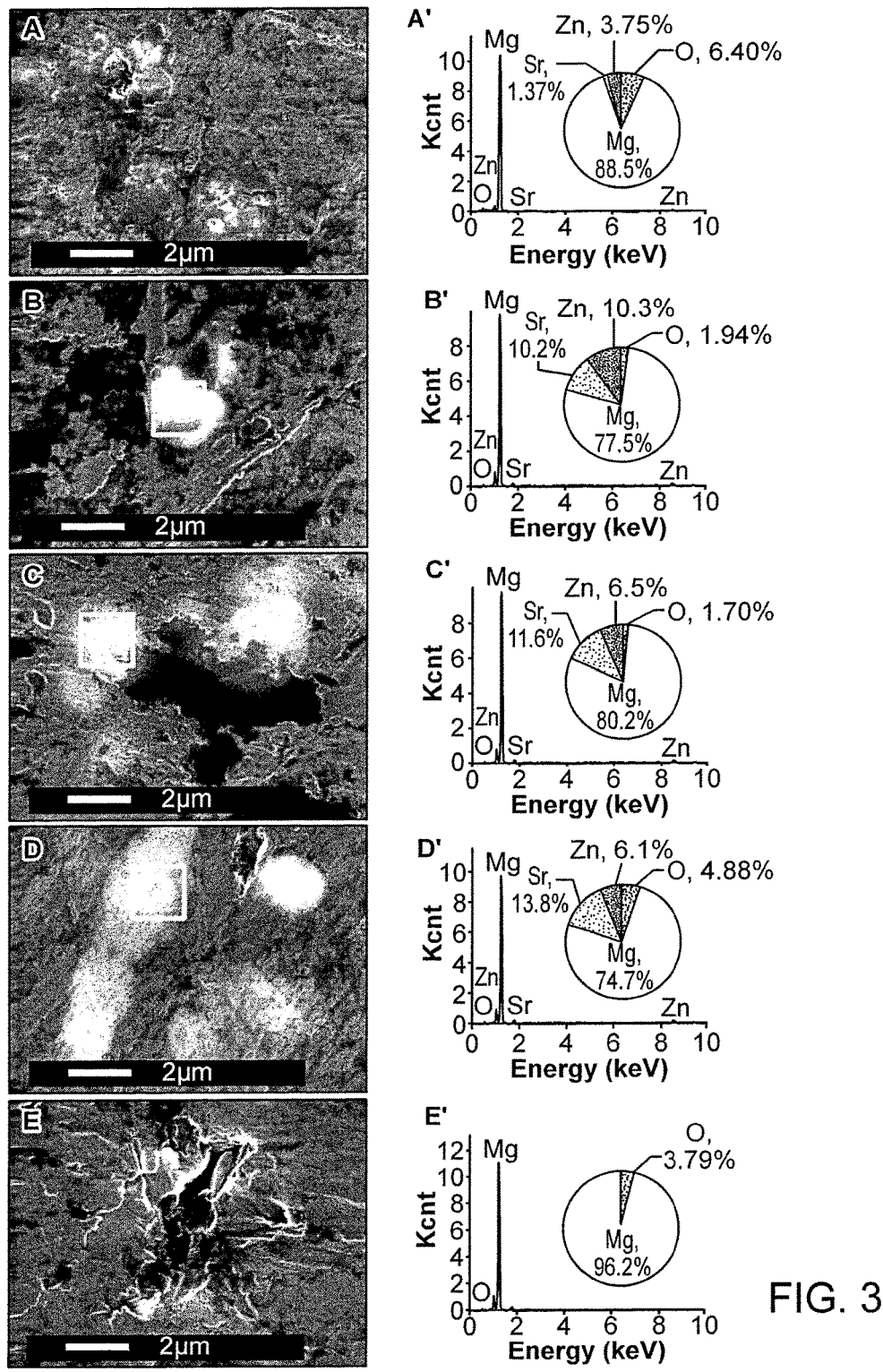
FIGS. 3(A)-(E) are scanning electron micrographs of (A) ZSr41A, (B) ZSr41B, (C) ZSr41C, (D) ZSr41 D, and (E) P-Mg after surface polishing at a magnification of 25,000×. (A'-E') EDS spectra and surface elemental composition (wt. %) of (A') ZSr41A, (B') ZSr41B highlighted area, (C') ZSr41C highlighted area, (D') ZSr41 D highlighted area, and (E') P-Mg. Accelerating voltage was 25 kV. Scale bars=2 µm.

Additionally, EDS analyses were also performed at 25,000× magnification in order to investigate the composition of the precipitates visible on the surfaces of the ZSr41 alloys (FIG. 3, A-E). EDS spectra of the highlighted area of precipitates (white particulate features) at the higher magnification (FIG. 3, A'-E' EDS spectra) indicated higher concentrations of Sr and Zn as compared with the composition detected on the overall surfaces of the alloys at the lower magnification. EDS analysis of the highlighted precipitates showed 13.79 wt. % Sr in ZSr41 D, 11.60 wt. % Sr in ZSr41C, and 10.24 wt % Sr in ZSr41B. In contrast, EDS analysis of ZSr41A at 25,000× magnification was done on the entire surface rather than a selected area due to the lack of precipitates and showed only 1.37 wt. % Sr.

In Vitro Degradation Results of ZSr41 Alloys

Figure 4:
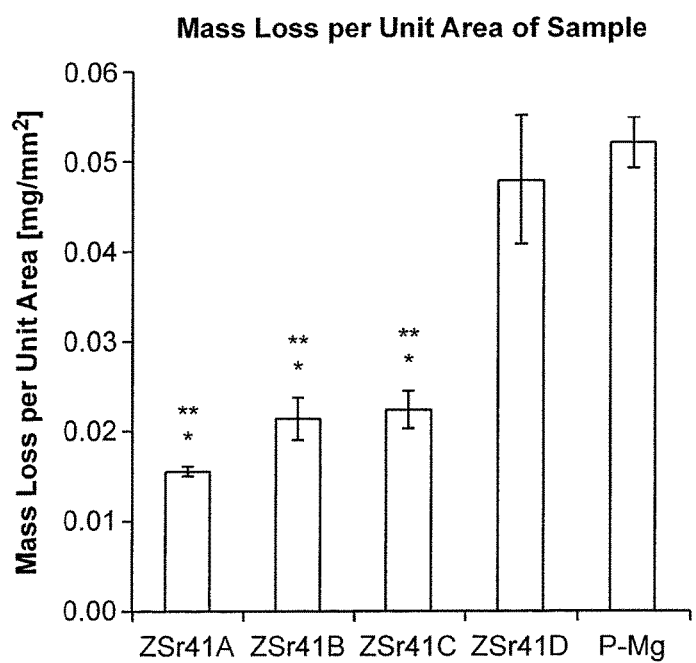
FIG. 4 is graph showing total mass loss per unit area of ZSr41 alloys and the control after culturing with H9 hESC for 72 hours. Values are mean±SEM; n=3; *p<0.05 compared to ZSr41 D; **p<0.05 compared to P-Mg.

Mass loss of Mg and ZSr41 alloys is an important measurement for quantification of the degradation rate when co-cultured with hESCs. Statistical analysis of the total mass loss per unit area over 72 hour degradation period indicated differences among the ZSr41 alloys and P-Mg according to ANOVA [$F(4, 10)=20.619$, $P<0.001$], as shown in FIG. 4. Post hoc pair-wise comparison tests revealed significantly less mass loss for ZSr41A, B, and C alloys when compared to P-Mg. Among the four ZSr41 alloys, ZSr41B and ZSr41C exhibited similar mass loss, and ZSr41 D showed significantly greater amount of mass loss when compared to the other compositions of ZSr41.

Figure 5:
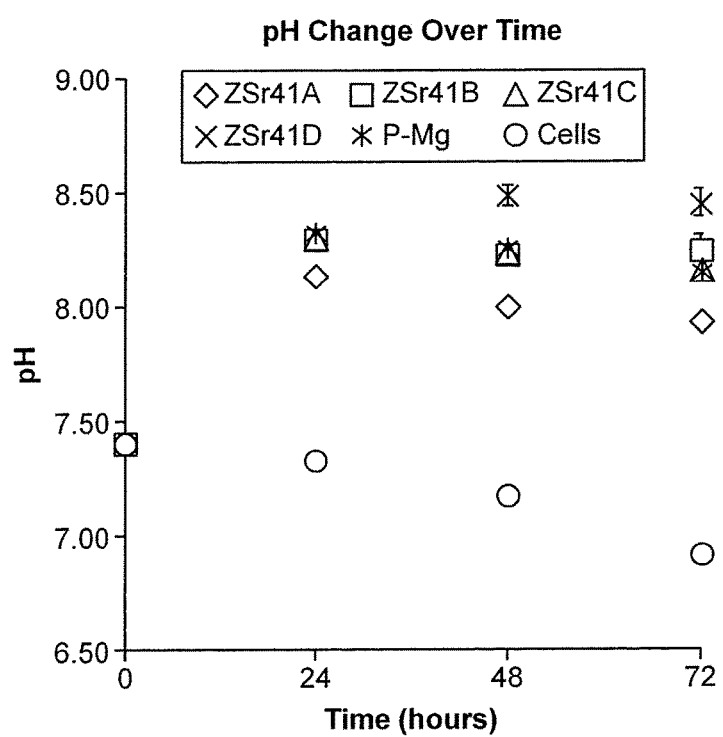
FIG. 5 is a graph showing change in pH of H9 hESC culture media as a result of degradation of ZSr41 alloys, P-Mg, and blank control (cells only). Values are mean±SEM; n=3; p<0.05 when comparing ZSr41A to other ZSr41 compositions, P-Mg, and blank control at all time points.

As Mg and Mg alloy degrade, soluble degradation products, for example, Mg ions ($Mg^{2+}$) and hydroxide ions ($OH^-$), are the other two important indicators of degradation rate. FIG. 5 shows pH change of cell culture media over time as a result of degradation of Mg and ZSr41 alloys. Analysis of the pH values of immersion media showed that ZSr41A degradation did not induce significant pH increase throughout all time intervals as compared with the other ZSr41 alloys and P-Mg. The pH increase of immersion media cultured with ZSr41 D was the highest among all the ZSr41 alloys and P-Mg tested. When comparing the pH change of the media containing ZSr41 alloys and P-Mg control with the blank control (cells and media only), the results showed that degradation products from P-Mg and ZSr41 alloys caused an increase in pH, while the blank control caused a decrease in pH. The decrease in pH for blank control was due to the metabolic activities of cells. Results also indicated a significant increase in pH during the initial 24 hour of culture as a result of initial degradation of ZSr41B, ZSr41C, and P-Mg.

Figure 6:
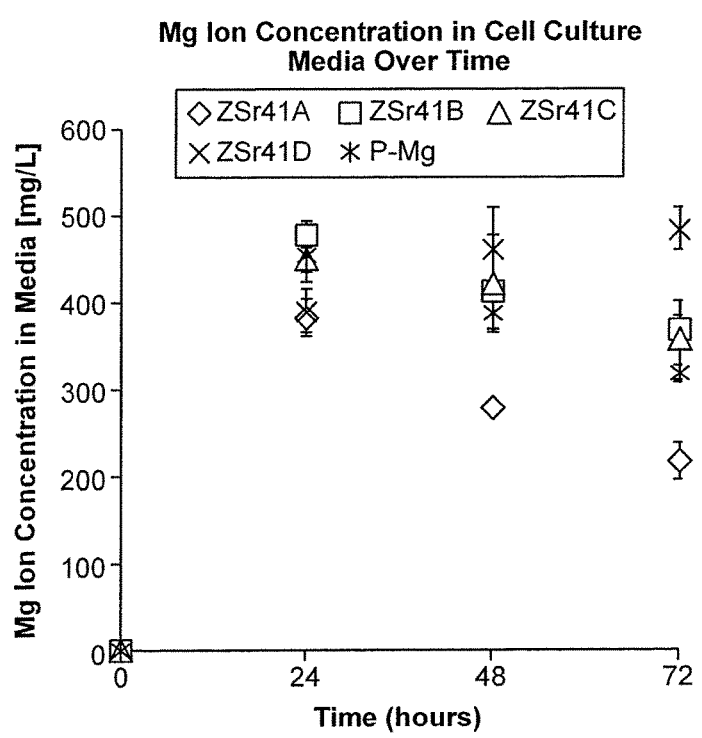
FIG. 6 is a graph showing the change of Mg ionic concentration in the cell culture media as a result of degradation of ZSr41 alloys and P-Mg. Mg ions in the media but not from Mg degradation were subtracted. Values are mean±SEM; n=3. Note: Mg/L=ppm.

FIG. 6 shows Mg ion concentration over time in the media cultured with Mg and ZSr41 alloys. The results indicated significant differences in the ICP-AES data of Mg ion concentration according to ANOVA [$F(4, 10)=13.69$, $p<0.05$]. Post hoc pair-wise comparison tests combined with Holm-Bonferroni correction only detected significant difference between ZSr41A and ZSr41 D. The media co-cultured with the ZSr41A alloy showed the lowest Mg ion concentration over the 72 hour immersion. The cell culture media in contact with the ZSr41 D alloy showed the greatest Mg ion concentration at the end of 72 hour culture period. Mg ion concentration in cell culture media in contact with most ZSr41 alloys and P-Mg increased to an initial maximum after 24 hour of immersion, and decreased after 48 and 72 hour immersion. The ZSr41B and ZSr41C alloys showed similar behavior to P-Mg in terms of Mg ion concentration. The daily measured Mg ion concentration in the media containing the ZSr41 was lowest for ZSr41A during the 48-72 hour interval with a value of 216.3 mg/L (8.9 mM), and was highest for ZSr41 D during the 48-72 hour interval with a value of 484.9 mg/L (19.9 mM). During the same 48-72 hour interval, ZSr41B and ZSr41C alloys showed a daily Mg ion concentration of 368.9 mg/L (15.2 mM), and 356.9 mg/L (14.7 mM), respectively. The range of daily measured Mg ion concentration for P-Mg was between 317.9 mg/L (13.1 mM) and 455.9 mg/L (18.8 mM).

Figure 7:
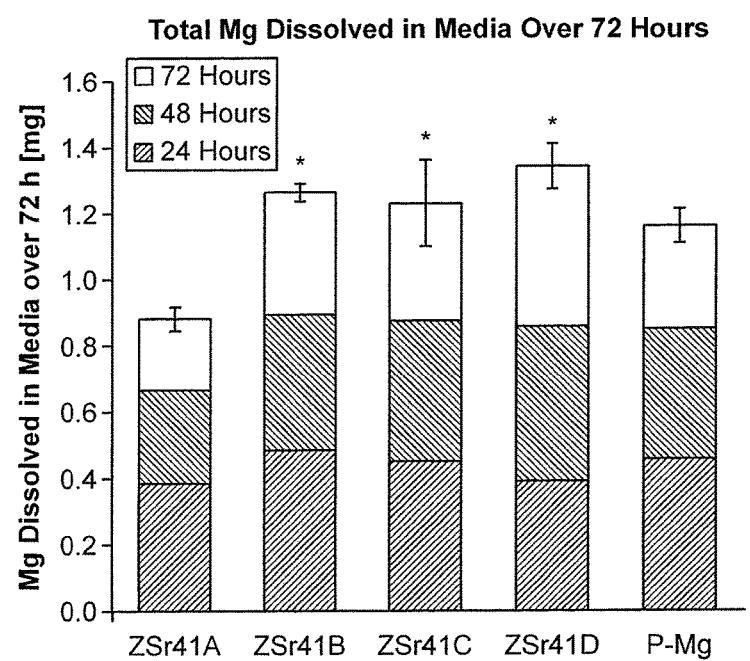
FIG. 7 is a chart showing total amount of Mg dissolved in the cell culture media when combining Mg ionic concentration measurements in the cell culture media at different time points as a result of degradation of ZSr41 alloys and P-Mg. Values are mean±SEM; n=3; *p<0.05 compared to ZSr41A.

FIG. 7 shows the total combined amount of Mg dissolved in the media during the 72 hour immersion. The total amount was calculated by multiplying the Mg ion concentration measured at each prescribed time interval by the volume of each sample analyzed and then by combining the totals from all time intervals. The results confirmed that the total Mg ions induced by ZSr41A alloy degradation was the lowest when compared to the other ZSr41 alloys and P-Mg. Additionally, the amounts of Sr and Zn dissolved in the media induced by the degradation of ZSr41 alloys were calculated based on the original Sr and Zn content in the ZSr41 alloy composition and the respective Mg concentrations from ICP-AES data. The results indicated that ZSr41A released the lowest amount of Sr ($3.4 \times 10-4$ mg, 48-72 hour interval) to the culture media while ZSr41 D released the highest amount of Sr ($7.7 \times 10-3$ mg, 48-72 hour interval). ZSr41B and ZSr1C showed a daily increase in the total amount of Sr dissolved in media of $1.9 \times 10-3$ mg and $3.8 \times 10-3$ mg, respectively. A similar trend was observed for the total amount of Zn dissolved in the media. ZSr41A showed the lowest daily Zn content increase ($9.0 \times 10-3$ mg) while ZSr41 D showed the highest ($2.1 \times 10-2$ mg). Both ZSr41B and ZSr1C showed a daily increase in the total amount of Zn dissolved in media of $1.5 \times 10-2$ mg.

In Vitro Cytocompatibility Results of ZSr41 Alloys with hESC

Figure 8:
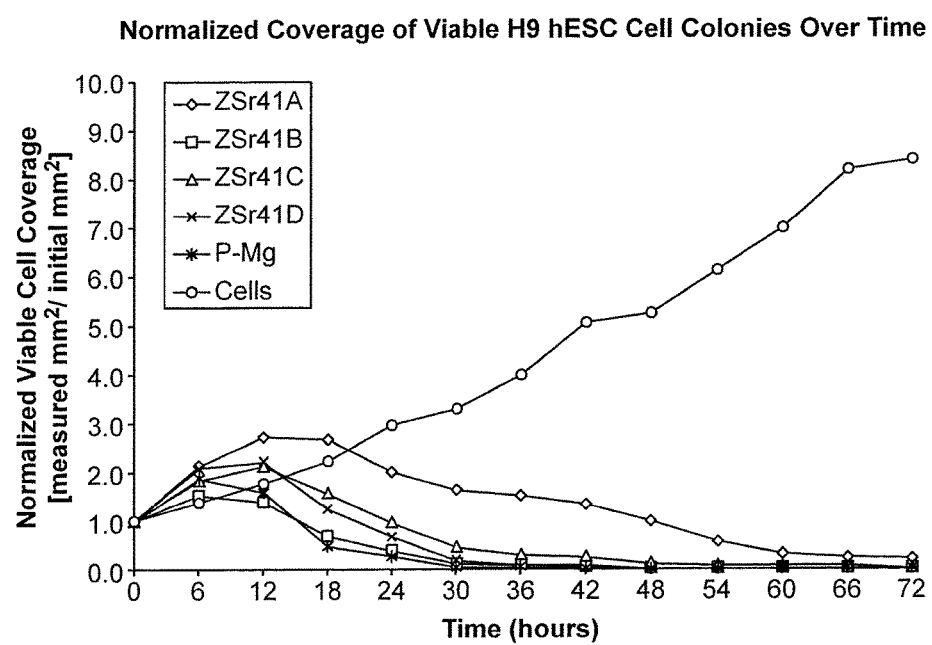
FIG. 8 is a graph showing the change of viable H9 hESC colony coverage over time after exposure to ZSr41 alloys and P-Mg degradation products as compared with the blank control (cells only). The viable cell coverage area at each time point was normalized by the initial cell coverage area at time zero.

Fluorescence images from the 72 hour cell culture study showed improved H9 hESC cytocompatibility with ZSr41 alloys compared with P-Mg, of which, ZSr41A alloy showed the best cytocompatibility overall. Normalized cell coverage of viable hESCs were quantified through analyses of the fluorescence and phase contrast images and the results are plotted in FIG. 8. Linear growth and proliferation of hESCs were observed in the control (cells only, no alloys). All four ZSr41 alloys and P-Mg control resulted in cell death at a different rate. The ZSr41 alloys prolonged the cell survival as compared with P-Mg control. After 30 hours of culture, all of the ZSr41 alloys exhibited coverage of viable cells. In contrast, almost no viable hESCs were visible in the co-culture with P-Mg at the 30 hour time interval. After 48 hours of culture, almost no viable cells were present in the co-cultures with ZSr41B, C and D, but some viable cells were still observed in the co-culture with ZSr41A. For example, at the end of the 72 hour study, ZSr41A alloy was the only one in which viable cells were still observed in its co-culture.

Figure 9:
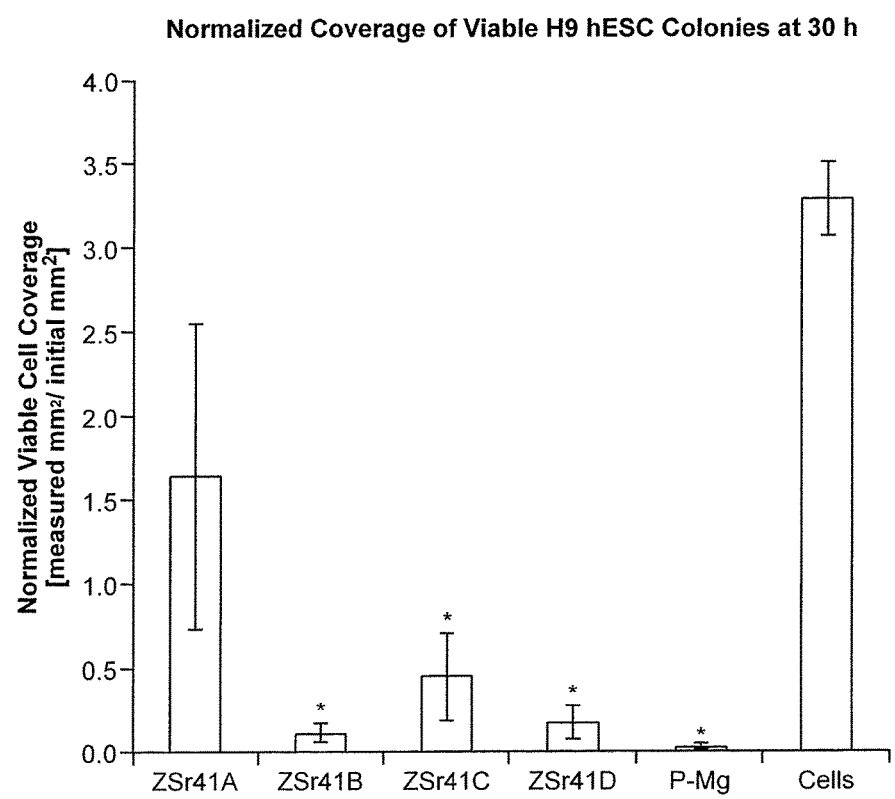
FIG. 9 is a chart showing normalized viable H9 hESC colony coverage after exposure to ZSr41 and P-Mg degradation products for 30 h as compared with the blank control (cells only). The viable cell coverage area was normalized by the initial cell coverage area at time zero. Values are mean±SEM; n=3; *p<0.05 when comparing ZSr41B, C, D, and PMg with the blank control (cells only). In accordance with an exemplary embodiment, no statistically significant difference was detected between ZSr41 and the blank control.

For example, the 30 hour time interval was chosen as the critical time point for further statistical analysis, because, at this time point, viable cells were still present in the co-culture with ZSr41 alloys while the amount of viable cells in the co-culture with P-Mg was nearly zero (FIG. 9). The Kruskal-Wallis test for non-parametric data showed significant differences in the means of viable cell coverage at 30 h [$X^2(5, N=18)=12.5041$, $p<0.05$]. The pair-wise comparison test revealed significantly less amounts of viable cells in the co-cultures with ZSr41B, C, and D alloys and P-Mg when compared to the blank control containing cells only. No statistically significant difference was detected between ZSr41A and the blank control at 30 hours.

Figure 10:
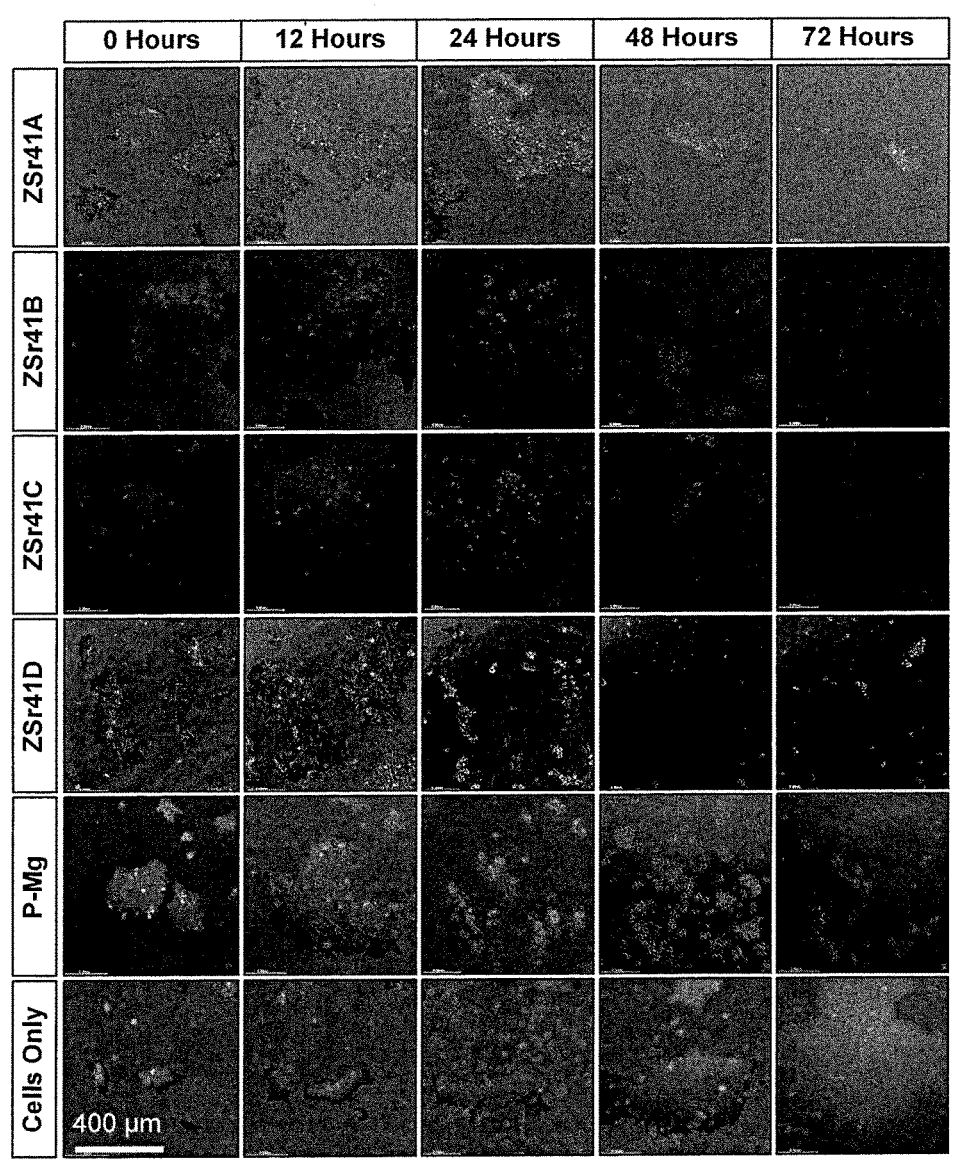
FIG. 10 is a montage of merged fluorescence and phase contrast images of H9 hESC colonies when co-cultured with ZSr41 alloys, P-Mg, and blank control (cells only) at the prescribed time intervals during the 72 h of cell culture. All images in the montage have the same magnification as shown by the 400 µm scale bar. ZSr41C ZSr41 D P-Mg Cells Only FIGS. 11 (A)-(E) are scanning electron micrographs of (A) ZSr41A, (B) ZSr41B, (C) ZSr41C, (D) ZSr41 D, and (E) P-Mg after 72-h degradation in hESC culture at a magnification of 1,000×. (A'-E') EDS spectra and surface elemental composition (wt. %) of (A') ZSr41A, (B') ZSr41B, (C') ZSr41C, (D') ZSr41 D, and (E') PMg. Accelerating voltage was 25 kV. Scale bars=50 µm.

Phase contrast and fluorescence images of hESCs in FIG. 10 indicate that ZSr41A was the only alloy where viable cells were observed in co-culture at the end of 72 h study. Comparison of the cell response to the ZSr41 alloys and P-Mg in FIG. 10 also showed a slightly better cell viability in the culture with the ZSr41C sample than that for the ZSr41B, D, and P-Mg samples. All Mg-based samples exhibited an initial increase in cell coverage followed by a steady decrease over time due to the following reasons. During the initial interval (0-14 h), the hESCs lost their closely packed organization and began to disperse. Thus, the area of viable cell coverage appeared larger. In comparison with the blank control with cells only, all Mg-based samples showed a decrease in percentage of viable cell coverage after initial period.

In summary, the cell viability results confirmed that the cytocompatibility of the ZSr41 alloys following this order, starting from the most cytocompatible: ZSr41A>ZSr41C>ZSr41B~ZSr41D>P-Mg.

Surface Morphology and Composition of ZSr41 Alloys after Cell Culture

Figure 11:
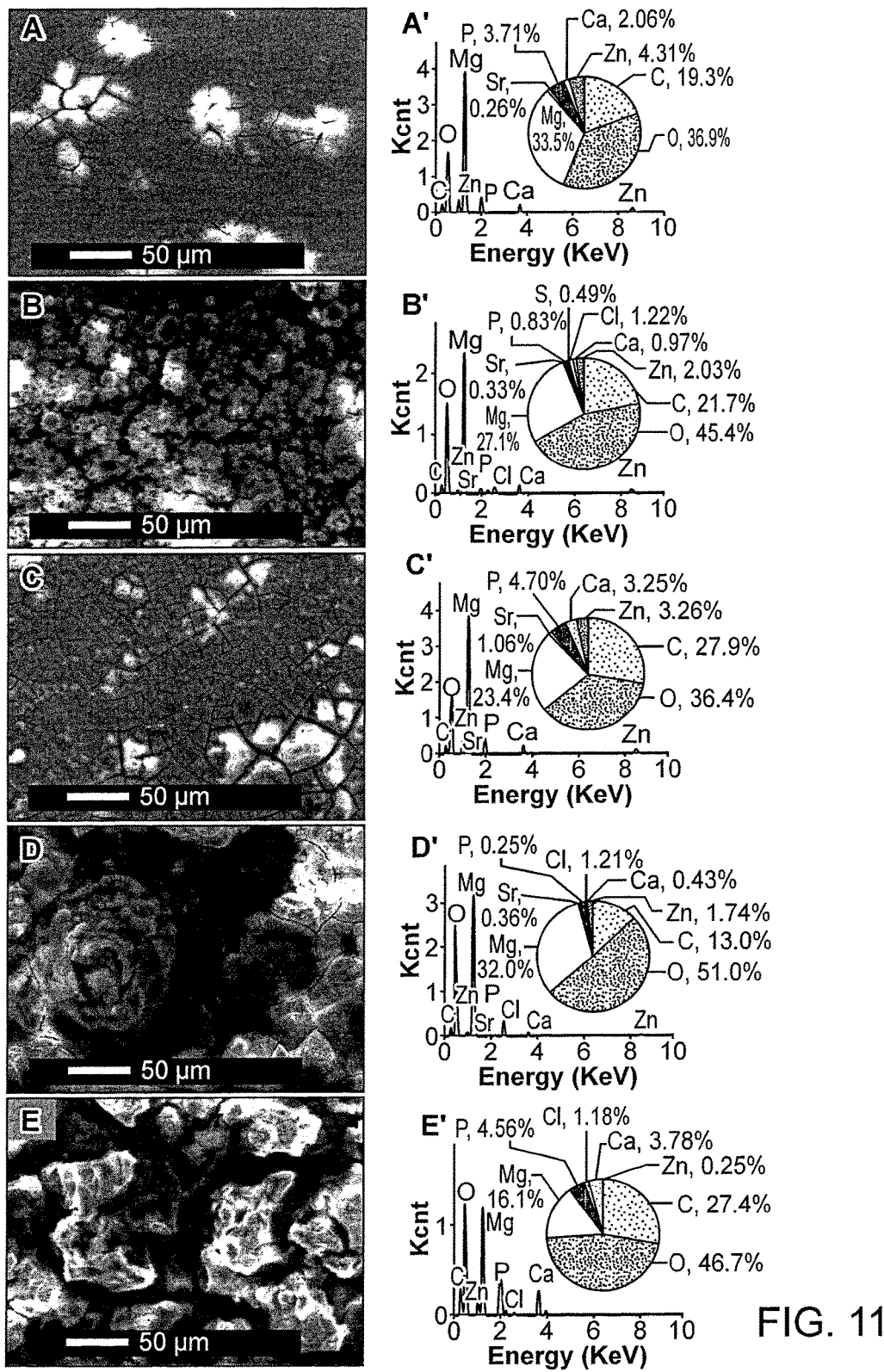
Figure 12:
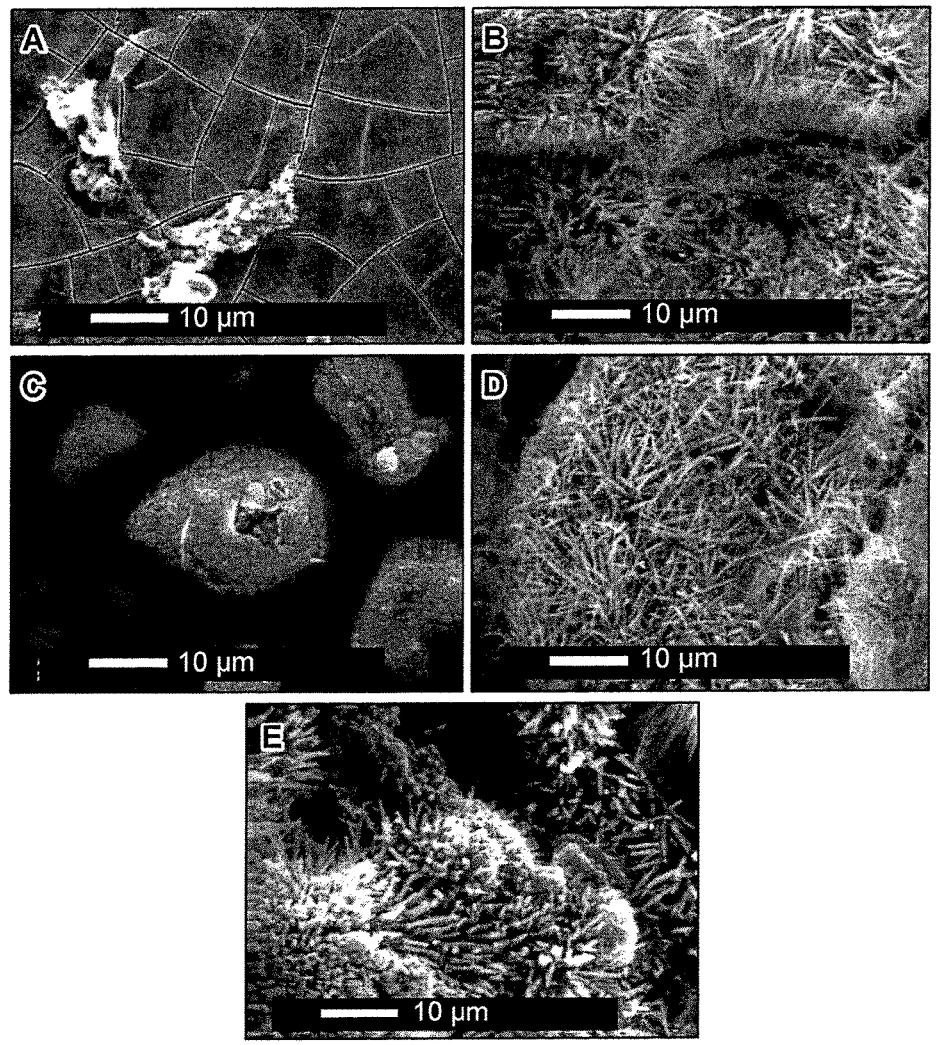
FIGS. 12 (A)-(E) are scanning electron micrographs of (A) ZSr41A, (B) ZSr41B, (C) ZSr41C, (D) ZSr41 D, and (E) P-Mg after 72-h degradation in hESC culture at a magnification of 5,000×. Accelerating voltage was 25 kV. Scale bars=10 µm.

The ZSr41 alloys were characterized after degradation in the cell culture, as shown in FIGS. 11 and 12. FIG. 11 shows the surface morphology and composition at 1,000× magnification where apparent degradation products were observed on all four ZSr41 alloys and P-Mg control. The ZSr41B, ZSr41 D, and P-Mg showed severe local corrosion and similar surface morphology. Less severe but localized corrosion along the grain boundaries was seen in ZSr41A and ZSr41C alloys. When compared to the grain size visible in P-Mg, the grains in the ZSr41 alloys were considerably smaller due to the refining effect of Sr. Among the ZSr41 alloys, the grain refinement effect of Sr was more pronounced in ZSr41A, ZSr41B and ZSr41C. FIG. 12 shows the surface morphology of ZSr41 alloys and P-Mg at 5,000× magnification. Formation of nano-sized needle-like surface features was identified on ZSr41B, ZSr41 D and P-Mg. SEM images at 5,000× magnification further confirmed that ZSr41A and ZSr41C alloys degraded in a similar fashion, for example, localized degradation at the grain boundaries.

The results of EDS analyses at 1,000× magnification indicated the presence of Chlorine (Cl) on the surface of the samples that exhibited more aggressive corrosion, namely ZSr41B, ZSr41 D and P-Mg (FIG. 11, A'-E' EDS spectra). In addition to Cl, other elements, including Mg, Zn, Sr, O, Ca, Phosphorus (P), and Carbon (C) were identified on the surface of the post-degraded samples. Ca, P and C and the increasing amount of O were precipitated from the cell culture media. Importantly, less amount of O (~36 wt. %) was found on the surfaces of ZSr41A and ZSr41C than that found on the surface of ZSr41B, ZSr41 D and P-Mg (~50 wt. %) which experienced more aggressive corrosion. EDS analyses also detected more Ca and P on the surface of ZSr41A and ZSr41C as compared with ZSr41B and ZSr41 D.

The present disclosure shows that degradation properties and cytocompatibility of Mg alloys are correlated design criteria and are important to consider in order to develop better Mg alloys to meet clinical needs. In this disclosure, four ZSr41 alloys were developed based on the beneficial effects of Zn and Sr on Mg alloy properties, and their degradation properties and cytocompatibility were investigated for medical applications. The ZSr41 alloys were co-cultured in vitro with hESCs to study the alloy degradation and interactions with cells in a physiologically simulated and sensitive environment.

The results of this disclosure shows how fast these ZSr41 Mg alloys degrade in the cell culture, and how cells responded to degradation products. For example, the ZSr41A alloy exhibited superior cytocompatibility and slower degradation as compared with ZSr41B, ZSr41C, ZSr41 D, and P-Mg. This superior cell response to ZSr41A can be attributed to its slower degradation. Specifically, ZSr41A showed less weight loss during 72 hours of co-culturing with hESCs, indicating a slower degradation. Furthermore, ZSr41A had a less pronounced effect on pH increase of cell culture media as compared with the other alloys and P-Mg. The ICP-AES results on Mg ion concentration further confirmed that less amount of Mg ions was solubilized in the cell culture media during the degradation of ZSr41A at each prescribed time, as compared to the other ZSr41 alloys and P-Mg control. In addition, the amount of Mg dissolved, and calculated values for Sr and Zn content in the cell culture media were well under the therapeutic levels that have been shown to be beneficial for humans. The slower release of soluble degradation products (Mg ions and hydroxide ions) from the ZSr41A alloy may contribute to the improved cell viability around ZSr41A.

The results of this disclosure showed that the viability of the H9 hESC colonies improved in the ZSr41A co-culture when compared to co-culture with the other ZSr41 alloys and P-Mg. The lower Mg ion concentration induced by slower degradation of ZSr41A was speculated to be one of the major contributing factors. Specifically, the results showed that viability of hESC colonies improved at Mg ion concentrations of 8.9-15.7 mM for ZSr41A, when compared with ZSr41B, C, D, and P-Mg, which had the concentration range of 13.1-19.9 mM. These results are in agreement with previous results reported in literature, for example, Feyerabend F, Fischer J, Holtz J, Witte F, Willumeit R, Drücker H, et al. Evaluation of short-term effects of rare earth and other elements used in magnesium alloys on primary cells and cell lines. Acta Biomaterialia 2010; 6:1834-42. Specifically, Feyerabend et al. suggested that the critical toxic range of extracellular Mg ion concentration was between 10-20 mM. However, due to the inherent differences between H9 hESC and HUCPV cells, the Mg ion concentration causing at least 50% reduction of cell viability was much lower for the H9 hESC (less than 19.9 mM) than HUCPV (73 mM). In other words, this comparison suggested a greater sensitivity associated with the h9-hESC model. However, in order to confirm the comparison of cytotoxicity evaluation between the models based on the H9 hESC and other cell lines (such as HUCPV), further in vitro studies would be beneficial if the exact same cell culture procedures were followed to evaluate the cytotoxicity of the same Mg alloy.

Addition of 0.15 wt. % Sr to Mg alloys (ZSr41A) resulted in formation of dispersed intermetallic phases and considerably improved degradation and cytocompatibility properties for clinical applications. However, continuous increase of the amount of Sr in Mg alloys (ZSr41B, ZSr41C and ZSr41 D) did not show evident benefits. It has been shown that the solubility of Sr in Mg is between 0.11 and 0.15 wt. % at 450° C. to 570° C. Additional studies have reported that addition of 0.1 to 0.3 wt. % Sr to AZ91, for example, see Liu S F, Liu L Y, Kang L G. Refinement role of electromagnetic stirring and strontium in AZ91 magnesium alloy. J Alloy Compd 2008; 450:546-50. Previous results indicated that ZSr41 with 1 wt. % Sr resulted in grain refinement of the alloy as a result of formation of Zn13 Sr, a dispersed intermetallic phase. During solidification, the Zn13Sr phase was pushed to the crystal growth edge of the primary α-Mg phase to restrain the growth of dendrites and led to grain refinement. The grain refinement behavior was clearly identifiable in SEM images of ZSr41A but not as obvious for ZSr41 D (1.5 wt. % Sr addition). The lack of grain refinement observed in ZSr41 D could be explained by the limited solubility of Sr in Mg and would agree with other studies which showed that addition of more than 0.7 wt. % Sr to an Mg-based alloy did not lead to grain refinement, but instead resulted in easier recrystallization that decreased mechanical properties of Mg-based alloys. In addition, as the amount of Sr added into Mg alloys increased, the corrosion rate of Mg alloys also accelerated due to the increased formation of galvanic couples between the Mg matrix and intermetallic Mg—Zn—Sr phases. These results indicated that the addition of Sr to the Mg—Zn alloy was critical and, specifically, 0.15 wt. % was optimal for the improvement of mechanical properties and corrosion properties of the material.

The degradation results of this disclosure also confirmed that the presence of ions and proteins in the physiological environment played an important role in the degradation mode and rate of ZSr41 alloys. For example, the presence of $Cl^-$ ions was only detected on the surfaces of ZSr41B, ZSr41 D and P-Mg by EDS, but not on ZSr41A and ZSr41C. Meanwhile, SEM images showed that ZSr41B, D and P-Mg exhibited more severe corrosion after 72 h cell culture, as compared with ZSr41A and ZSr41C. These results matched the literature report that Cl ions ($Cl^-$) contributed to severe pitting corrosion in Mg alloys due to the formation of highly soluble magnesium chloride. The cytocompatibility results showed a similar trend as the degradation results, i.e., prolonged and improved cell viability in the co-cultures with ZSr41A and ZSr41C as compared with ZSr41B, ZSr41 D and P-Mg. The correlation between the degradation and cytocompatibility results was apparent when considering them together.

In summary, this disclosure shows that the degradation properties and cytocompatibility of the Mg—Zn—Sr ternary alloys were highly dependent on the amounts of Sr added. For example, the ZSr41A alloy with 0.15 wt. % Sr was a promising candidate for biomedical applications due to its slower degradation and improved cell viability. However, further in vitro studies with primary cell cultures and in vivo studies in an actual implant environment are necessary to obtain a more thorough cytocompatibility assessment prior to translating to clinical applications.

Mg—Zn—Sr ternary alloys were developed and studied for the first time for biomedical implant applications. The results showed enhanced cytocompatibility with the ZSr41A alloy compared to the other ZSr41 alloys studied. Enhanced cell viability with ZSr41A alloy was due to its slower degradation, as indicated by less weight loss, less pH increase in media, and lower Mg ion concentration detected in media. For example, the slower degradation of ZSr41A alloy can be attributed to the grain refining effects of Sr and the effects of Zn and Sr on corrosion resistance. In this disclosure, the hESC culture model was used due to its inherent sensitivity to degradation products. The H9 hESC model can serve as an initial in vitro screening model to demonstrate the biocompatibility and biosafety of novel biomaterials at the early stage.

It will be understood that the foregoing description is of the preferred embodiments, and is, therefore, merely representative of the article and methods of manufacturing the same. It can be appreciated that many variations and modifications of the different embodiments in light of the above teachings will be readily apparent to those skilled in the art. Accordingly, the exemplary embodiments, as well as alternative embodiments, may be made without departing from the spirit and scope of the articles and methods as set forth in the attached claims.

What is claimed is:

1. A medical implant consisting of:
   a biodegradable and cytocompatible magnesium-zinc-strontium alloy; and
   a weight percent of zinc being 4.0 to 6.0, a weight percent of strontium being 0.01 to 0.15, and a balance of the medical implant being magnesium.

2. The medical implant according to claim 1, wherein the implant is an orthopedic, dental, plastic surgical or vascular implant.

3. The medical implant according to claim 2, wherein the orthopedic, dental, plastic surgical or vascular implant is a bone screw, a bone anchor, a tissue staple, a suture, a craniofacial, maxillofacial reconstruction plate, a fastener, a reconstructive dental implant, a medical fixation device, or an embolization material.

4. The medical implant according to claim 1, wherein the implant is composed of only the biodegradable magnesium-zinc-strontium alloy.

5. The medical implant according to claim 1, comprising:
   a coating layer composed of the biodegradable magnesium-zinc-strontium alloy on a surface of the medical implant.

6. A medical implant consisting of:
   a biodegradable and cytocompatible magnesium-zinc-strontium alloy, wherein the biodegradable and cytocompatible magnesium-zinc-strontium alloy has a weight percent composition of Zn and Sr as follows: $4.0 \leq Zn \leq 6.0$ wt. %, $0.01 \leq Sr \leq 0.15$ wt. %, and a balance of the medical implant being magnesium; and
   wherein the implant is an orthopedic, dental, plastic surgical or vascular implant.

7. The medical implant according claim 6, wherein the orthopedic, dental, plastic surgical or vascular implant is a bone screw, a bone anchor, a tissue staple, a suture, a craniofacial, maxillofacial reconstruction plate, a fastener, a reconstructive dental implant, a medical fixation device, or an embolization material.

8. The medical implant according to claim 6, comprising:
   a coating layer composed of the biodegradable magnesium-zinc-strontium alloy on a surface of the medical implant.

9. The medical implant according to claim 6, wherein the biodegradable and cytocompatible magnesium-zinc-strontium alloy has a weight percent composition of 95.85 wt. % Mg, 4 wt. % Zn, and 0.15 wt. % Sr.

10. The medical implant according to claim 6, wherein the biodegradable and cytocompatible magnesium-zinc-strontium alloy has a weight percent composition of 94.5-95.85 wt. % Mg, 4 wt. % Zn, and 0.01-0.15 wt. % Sr.

11. A medical implant consisting of:
    a biodegradable and cytocompatible magnesium-zinc-strontium alloy, wherein the biodegradable and cytocompatible magnesium-zinc-strontium alloy has a weight percent of 91-95.84 wt. % Mg, 4.0-6.0 wt. % Zn, and 0.01-0.015 wt. % Sr.

12. The medical implant according to claim 11, wherein the implant is an orthopedic, dental, plastic surgical or vascular implant.

13. The medical implant according claim 12, wherein the orthopedic, dental, plastic surgical or vascular implant is a bone screw, a bone anchor, a tissue staple, a suture, a craniofacial, maxillofacial reconstruction plate, a fastener, a reconstructive dental implant, a medical fixation device, or an embolization material.

14. The medical implant according to claim 11, comprising:
    a coating layer composed of the biodegradable magnesium-zinc-strontium alloy on a surface of the medical implant or device.

* * * * *